United States Patent
Wu et al.

(10) Patent No.: US 10,011,822 B2
(45) Date of Patent: Jul. 3, 2018

(54) PHYTASE HAVING IMPROVED THERMOSTABILITY

(71) Applicant: Dongguan APAC Biotechnology CO., Ltd., DongGuan (CN)

(72) Inventors: Tzu-Hui Wu, Taipei (TW); Ya-Shan Cheng, Taipei (TW); Hui-Lin Lai, Taipei (TW); Cheng-Yen Lin, Taipei (TW); Tsung-Yu Ko, Taipei (TW); Jian-Wen Huang, Taipei (TW); Chun-Chi Chen, Taipei (TW); Rey-Ting Guo, Taipei (TW)

(73) Assignee: DONGGUAN APAC BIOTECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 15/436,434

(22) Filed: Feb. 17, 2017

(65) Prior Publication Data
US 2017/0240872 A1   Aug. 24, 2017

(30) Foreign Application Priority Data
Feb. 18, 2016   (TW) .............................. 105104689 A

(51) Int. Cl.
| | |
|---|---|
| *C12N 9/16* | (2006.01) |
| *C12P 21/06* | (2006.01) |
| *C12P 19/34* | (2006.01) |
| *C07H 21/04* | (2006.01) |
| *C07K 1/00* | (2006.01) |
| *C12N 9/14* | (2006.01) |

(52) U.S. Cl.
CPC ................ *C12N 9/16* (2013.01); *C12N 9/14* (2013.01); *C12Y 301/03002* (2013.01); *C12Y 301/03008* (2013.01); *C12Y 301/03026* (2013.01)

(58) Field of Classification Search
CPC .... C12N 9/14; C12N 9/16; C12Y 301/03002; C12Y 301/03008; C12Y 301/03026
USPC ........... 435/196, 69.1, 91.1; 536/23.1, 23.2; 530/350
See application file for complete search history.

(56) References Cited

FOREIGN PATENT DOCUMENTS

| TW | 201504260 A | 2/2015 |
|---|---|---|
| WO | 2007/112739 A1 | 10/2007 |
| WO | 2001/117396 A2 | 9/2011 |

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Long Liu et al., In Silico Rational Design and Systems Engineering of Disulfide Bridges in the Catalytic Domain of an Alkaline α-Amylase from Alkalimonas amylolytica to Improve Thermostability, AEM Journals ASM.org, Feb. 2014, vol. 80 No. 3, American Society for Microbiology, United States of America.

* cited by examiner

*Primary Examiner* — Ganapathiram Raghu
(74) *Attorney, Agent, or Firm* — Kirton McConkie; Evan R. Witt

(57) ABSTRACT

A phytase having improved thermostability is disclosed. The phytase has a modified amino acid sequence of SEQ ID NO: 2, wherein the modification is one of mutations A to D. The mutation A is to substitute amino acids at positions 143 and 262 with cysteine, the mutation B is to substitute amino acids at positions 259 and 312 with cysteine, the mutation C is to substitute amino acids at positions 205 and 257 with cysteine, and the mutation D is to substitute amino acids at positions 264 and 309 with cysteine.

12 Claims, 10 Drawing Sheets cagagtgagcctgagttgaaactggaatccgttgtcatcgtctctagacatggtgttagagcaccaaccaagttcacccaacttatgcaa
 Q  S  E  P  E  L  K  L  E  S  V  V  I  V  S  R  H  G  V  R  A  P  T  K  F  T  Q  L  M  Q gatgtcacccagacgcttggccaacctggccagtcaagctgggtgaattgacacctagaggttgtgagctcattgcttacttgggtcac
 D  V  T  P  D  A  W  P  T  W  P  V  E  L  G  E  L  T  P  G  C  E  L  I  A  Y  L  G  H tactggagacagcgtcttgttgccgacgaattgttgcctaagtgtggttgtccacaatctggtcaagtagctattattgctgacgtcgac
 Y  W  R  Q  R  L  V  A  D  E  L  L  P  K  C  G  C  P  Q  S  G  Q  V  A  I  I  A  D  V  D gaaagaacccgtaagacaggtgaatgtttcgccgccggtcttgctcctgactgtgccattaccgtccaccatcaagctgacacttcttct
 E  R  T  R  K  T  G  E  C  F  A  A  G  L  A  P  D  C  A  I  T  V  H  H  Q  A  D  T  S  S ccagatccattgttcaaccctttgaagactggtgtttgccaattggacgttgctaacgttactagatgtatcttggaaagagctggagga
 P  D  P  L  F  N  P  L  K  T  G  V  C  Q  L  D  V  A  N  V  T  R  C  I  L  E  R  A  G  G tctattgctgacttcaccggtcactaccagactgccttcagagagttggaaagagttcttaacttcccacaatccaacttgtgccttaag
 S  I  A  D  F  T  G  H  Y  Q  T  A  F  R  E  L  E  R  V  L  N  F  P  Q  S  N  L  C  L  K cgtgagaagcaagacgaatcctgttccttgactcaagcattaccatctgagttgaaggtctccgccgacaacgtctctttgaccggtgct
 R  E  K  Q  D  E  S  C  S  L  T  Q  A  L  P  S  E  L  K  V  S  A  D  N  V  S  L  T  G  A gtcagcttggcttccatgttgactgaaatctttcttctgcaacaagctcaaggtatgcctgagccaggttggggtagaatcaccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattcgatttgctgcagagaactccatgtgttgctagatccagagccacccca
 H  Q  W  N  T  L  L  S  L  H  N  A  Q  F  D  L  L  Q  R  T  P  C  V  A  R  S  R  A  T  P ttgttggacttgatcaagactgctttgactcctcacccacctcaaaagcaagcctacggtgttaccttgccacttctgtcttgttcatt
 L  L  D  L  I  K  T  A  L  T  P  H  P  P  Q  K  Q  A  Y  G  V  T  L  P  T  S  V  L  F  I gccggtcacgatactaacttggcaaatctcggcggtgctttggagttgaactggactcttcctggtcaacctgataacactccaccaggt
 A  G  H  D  T  N  L  A  N  L  G  G  A  L  E  L  N  W  T  L  P  G  Q  P  D  N  T  P  P  G ggtgagctcgttttcgaaagatgcgtagactatctgataaactctcaatggattcaggtttcgttggtcttccaaactttgcagcagatg
 G  E  L  V  F  E  R  W  P  L  D  N  D  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
 R  D  K  T  P  L  S  L  N  T  P  P  G  E  V  K  L  T  L  A  G  C  E  E  R  N  A  Q  G  M tgttccttggctggtttcactcaaatcgttaacgaagctagaatcccagcttgttccttgtagtaa  -SEQ ID NO. 1
 C  S  L  A  G  F  T  Q  I  V  N  E  A  R  I  P  A  C  S  L  *  *   -SEQ ID NO. 2

FIG. 1

| SEQ ID NO. | Primer | Sequence (5'-3') |
|---|---|---|
| 3 | AppA-A1-F | GCTAACGTTACTAGATGTATCTTGGAAAGAGCT |
| 4 | AppA-A1-R | AGCTCTTTCCAAGATACATCTAGTAACGTTAGC |
| 5 | AppA-A2-F | CTGCAGAGAACTCCATGTGTTGCTAGATCCAGA |
| 6 | AppA-A2-R | TCTGGATCTAGCAACACATGGAGTTCTCTGCAG |
| 7 | AppA-B1-F | TTCGATTTGCTGCAGTGTACTCCAGAGGTTGCT |
| 8 | AppA-B1-R | AGCAACCTCTGGAGTACACTGCAGCAAATCGAA |
| 9 | AppA-B2-F | TTGGCAAATCTCGGCTGTGCTTTGGAGTTGAAC |
| 10 | AppA-B2-R | GTTCAACTCCAAAGCACAGCCGAGATTTGCCAA |
| 11 | AppA-C1-F | GTCTCCGCCGACAACTGTTCTTTGACCGGTGCT |
| 12 | AppA-C1-R | AGCACCGGTCAAAGAACAGTTGTCGGCGGAGAC |
| 13 | AppA-C2-F | GCTCAATTCGATTTGTGTCAGAGAACTCCAGAG |
| 14 | AppA-C2-R | CTCTGGAGTTCTCTGACACAAATCGAATTGAGC |
| 15 | AppA-D1-F | AGAACTCCAGAGGTTTGTAGATCCAGAGCCACC |
| 16 | AppA-D1-R | GGTGGCTCTGGATCTACAAACCTCTGGAGTTCT |
| 17 | AppA-D2-F | GATACTAACTTGGCATGTCTCGGCGGTGCTTTG |
| 18 | AppA-D2-R | CAAAGCACCGCCGAGACATGCCAAGTTAGTATC |
| 19 | AppA-A2+B1-F | TTCGATTTGCTGCAGTGTACTCCATGTGTTGCTAGATCCAGA |
| 20 | AppA-A2+B1-R | TCTGGATCTAGCAACACATGGAGTACACTGCAGCAAATCGAA |
| 21 | AppA-A2+D1-F | CTGCAGAGAACTCCATGTGTTTGTAGATCCAGAGCCACC |
| 22 | AppA-A2+D1-R | GGTGGCTCTGGATCTACAAACACATGGAGTTCTCTGCAG |

FIG. 3

```
cagagtgagcctgagttgaaactggaatccgttgtcatcgtctctagacatggtgttagagcaccaaccaagttcacccaacttatgcaa
 Q  S  E  P  E  L  K  L  E  S  V  V  I  V  S  R  H  G  V  R  A  P  T  K  F  T  Q  L  M  Q gatgtcacccagacgcttggccaacctggccagtcaagctgggtgaattgacaccaagaggttgtgagctcattgcttacttgggtcac
 D  V  T  P  D  A  L  A  N  L  A  S  Q  A  G  E  L  T  P  R  G  C  E  L  I  A  Y  L  G  H tactggagacagcgtcttgttgccgacgaattgttgcctaagtgtggttgtccacaatctggtcaagtagctattattgctgacgtcgac
 Y  W  R  Q  R  L  V  A  D  E  L  L  P  K  C  G  C  P  Q  S  G  Q  V  A  I  I  A  D  V  D gaaagaaccgtaagacaggtgaatgtttcgccgccggtcttgctcctgactgtgccattaccgttcaccatcaagctgacacttcttct
 E  R  T  K  T  G  E  C  F  A  A  G  L  A  P  D  C  A  I  T  V  H  H  Q  A  D  T  S  S ccagatccattgttcaaccctttgaagactggtgtttgccaattggacgttgctaacgttactagatgtatcttggaaagagctggagga
 P  D  P  L  F  N  P  L  K  T  G  V  C  Q  L  D  V  A  N  V  T  R  C  I  L  E  R  A  G  G tctattgctgacttcaccggtcactaccagactgccttcagagagttggaaagagttcttaacttcccacaatccaacttgtgccttaag
 S  I  A  D  F  T  G  H  Y  Q  T  A  F  R  E  L  E  R  V  L  N  F  P  Q  S  N  L  C  L  K cgtgagaagcaagacgaatcctgttccttgactcaagcattaccatctgagttgaaggtctccgccgacaacgtctctttgaccggtgct
 R  E  K  Q  D  E  S  C  S  L  T  Q  A  L  P  S  E  L  K  V  S  A  D  N  V  S  L  T  G  A gtcagcttggcttccatgttgactgaaatctttcttctgcaacaagctcaaggtatgcctgagccaggttggggtagaatcaccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattcgatttgctgcagagaactccatgtgttgctagatccagagccacccca
 H  Q  W  N  T  L  L  S  L  H  N  A  Q  F  D  L  L  Q  R  T  P  C  V  A  R  S  R  A  T  P ttgttggacttgatcaagactgctttgactcctcacccacctcaaaagcaagcctacggtgttaccttgccacttctgtcttgttcatt
 L  L  D  L  I  K  T  A  L  T  P  H  P  P  Q  K  Q  A  Y  G  V  T  L  P  T  S  V  L  F  I gccggtcacgatactaacttggcaaatctcggcggtgctttggagttgaactggactcttcctggtcaacctgataacactccaccaggt
 A  G  H  D  T  N  L  A  N  L  G  G  A  L  E  L  N  W  T  L  P  G  Q  P  D  N  T  P  P  G ggtgagctcgttttcgaaagatggcgtagactatctgataactctcaatggattcaggtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
 R  D  K  T  P  L  S  L  N  T  P  P  G  E  V  K  L  T  L  A  G  C  E  E  R  N  A  Q  G  M tgttccttggctggtttcactcaaatcgttaacgaagctagaatcccagcttgttccttgtagtaa    -SEQ ID NO. 23
 C  S  L  A  G  F  T  Q  I  V  N  E  A  R  I  P  A  C  S  L  *  *      -SEQ ID NO. 24
```

FIG. 4

```
cagagtgagcctgagttgaaactggaatccgttgtcatcgtctctagacatggtgttagagcaccaaccaagttcacccaacttatgcaa
 Q  S  E  P  E  L  K  L  E  S  V  V  I  V  S  R  H  G  V  R  A  P  T  K  F  T  Q  L  M  Q gatgtcacccagacgcttggccaacctggccagtcaagctgggtgaattgacacctagaggttgtgagctcattgcttacttgggtcac
 D  V  T  P  D  A  W  P  T  W  P  V  K  L  G  E  L  T  P  P  G  C  E  L  I  A  Y  L  G  H tactggagacagcgtcttgttgccgacgaattgttgcctaagtgtggttgtccacaatctggtcaagtagctattattgctgacgtcgac
 Y  W  R  Q  R  L  V  A  D  E  L  L  P  K  C  G  C  P  Q  S  G  Q  V  A  I  I  A  D  V  D gaaagaacccgtaagacaggtgaatgtttcgcgccggtcttgctcctgactgtgccattaccgtcaccatcaagctgacacttcttct
 E  R  T  R  K  T  G  E  C  F  A  A  G  L  A  P  D  C  A  I  T  V  H  H  Q  A  D  T  S  S ccagatccattgttcaaccctttgaagactggtgtttgccaattggacgttgctaacgttactagagctatcttggaagagctggagga
 P  D  P  L  F  N  P  L  K  T  G  V  C  Q  L  D  V  A  N  V  T  R  A  I  L  E  R  A  G  G tctattgctgacttcacggtcactaccagactgccttcagagagttggaaagagttcttaacttcccacaatccaacttgtgccttaag
 S  I  A  D  F  T  G  H  Y  Q  T  A  F  R  E  L  P  V  L  N  F  P  Q  S  N  L  C  L  K cgtgagaagcaagacgaatcctgttccttgactcaagcattaccatctgagttgaaggtctccgccgacaacgtctctttgaccggtgct
 R  E  K  Q  D  E  S  C  S  L  T  Q  A  L  P  S  E  L  K  V  S  A  D  N  V  S  L  T  G  A gtcagcttggcttccatgttgactgaaatctttcttctgcaacaagctcaaggtatgcctgagccaggttggggtagaatcaccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattcgatttgctgcadtgtactccagaggttgctagatccagagccacccca
 H  Q  W  N  T  L  L  S  L  H  N  A  Q  F  D  L  L  Q  C  T  F  E  V  A  R  S  R  A  P ttgttggacttgatcaagactgctttgactcctcacccacctcaaaagcaagcctacggtgttaccttgccaacttctgtcttgttcatt
 L  L  D  L  I  K  T  A  L  T  P  H  P  P  Q  K  Q  A  Y  G  V  T  L  P  T  S  V  L  F  I gccggtcacgatactaacttggcaaatctcggdtgtgctttggagttgaactggactcttcctggtcaacctgataacactccaccaggt
 A  G  H  D  T  N  L  A  N  L  G  C  A  L  E  L  N  W  T  L  P  G  Q  P  D  N  T  P  P  G ggtgagctcgttttcgaaagatggcgtagactatctgataactctcaatgattcaggtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgacctggctggatgtgaagagagaaatgctcagggtatg
 R  D  K  T  P  L  S  L  N  T  P  P  G  E  V  K  L  T  L  A  G  C  E  R  H  A  Q  G  M tgttccttggctggtttcactcaaatcgttaacgaagctagaatcccagcttgttccttgtagtaa       -SEQ ID NO. 25
 C  S  L  A  G  F  T  Q  I  V  N  E  A  R  I  P  A  C  S  L  *  *          -SEQ ID NO. 26
```

FIG. 5

```
cagagtgagcctgagttgaaactggaatccgttgtcatcgtctctagacatggtgttagagcaccaaccaagttcacccaacttatgcaa
 Q  S  E  P  E  L  K  L  E  S  V  V  I  V  S  R  H  G  V  R  A  P  T  K  F  T  Q  L  M  Q gatgtcaccccagacgcttggccaacctggccagtcaagctgggtgaattgacacctagaggttgtgagctcattgcttacttgggtcac
 D  V  T  P  D  A  W  P  T  W  P  V  K  L  G  E  L  T  P  K  G  C  E  L  I  A  Y  L  G  H tactggagacagcgtcttgttgccgacgaattgttgcctaagtgtggttgtccacaatcggtcaagtagctattattgctgacgtcgac
 Y  W  R  Q  R  L  V  A  D  E  L  L  P  K  C  G  C  P  Q  S  G  Q  V  A  I  I  A  D  V  D gaaagaacccgtaagacaggtgaatgtttcgccgccggtcttgctcctgactgtgccattaccgttcaccatcaagctgacacttcttct
 E  R  T  R  K  T  G  E  C  F  A  A  G  L  A  P  D  C  A  I  T  V  H  H  Q  A  D  T  S  S ccagatccattgttcaaccctttgaagactggtgtttgccaattggacgttgctaacgttactagagctatcttggaaagagctggagga
 P  D  P  L  F  N  P  L  K  T  G  V  C  Q  L  D  V  A  N  V  T  R  A  I  L  E  R  A  G  G tctattgctgacttcacggtcactaccagactgccttcagagagttggaaagagttcttaacttcccacaatccaacttgtgccttaag
 S  I  A  D  F  T  G  H  Y  Q  T  A  F  R  E  L  E  R  V  L  N  F  Q  S  N  L  C  L  K cgtgagaagcaagacgaatcctgttccttgactcaagcattaccatctgagttgaaggtctccgccgacaacgttctttgaccggtgct
 P  E  K  Q  D  E  S  C  S  L  T  Q  A  L  P  S  E  L  K  V  S  A  D  N  C  S  L  T  G  A gtcagcttggcttccatgttgactgaaatctttcttctgcaacaagctcaaggtatgcctgagccaggtggggtagaatccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattcgatttgtgtcagagaactccagaggttgctagatccagagccacccca
 H  Q  W  N  T  L  L  S  L  H  N  A  Q  F  D  L  C  Q  R  T  P  E  V  A  R  S  R  A  T  P ttgttggacttgatcaagactgctttgactcctcacccacctcaaaagcaagctacggtgttaccttgccacttctgtcttgttcatt
 L  L  D  L  I  K  T  A  L  T  P  H  P  P  Q  K  Q  A  Y  G  V  T  L  P  T  S  V  L  F  I gccggtcacgatactaacttggcaaatctcggcggtgctttggagttgaactggactcttcctggtcaacctgataacactccaccaggt
 A  G  H  D  T  N  L  A  N  L  G  G  A  L  E  L  N  W  T  L  P  G  Q  P  D  N  T  P  P  G ggtgagctcgttttcgaaagatggcgtagactatctgataactctcaatggattcaggtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgacttggctggatgtgaagagagaaatgctcagggtatg
 R  D  K  T  P  L  S  L  N  T  P  P  G  E  V  K  L  T  W  L  A  G  C  E  E  N  A  Q  G  M tgttccttggctggtttcactcaaatcgttaacgaagctagaatcccagcttgttccttgtagtaa            -SEQ ID NO. 27
 C  S  L  A  G  F  T  Q  I  V  N  E  A  R  I  P  A  C  S  L  *  *               -SEQ ID NO. 28
```

FIG. 6 cagagtgagcctgagttgaaactggaatccgttgtcatcgtctctagacatggtgttagagcaccaaccaagttcacccaacttatgcaa
Q  S  E  P  E  L  K  L  E  S  V  V  I  V  S  R  H  G  V  R  A  P  T  K  F  T  Q  L  M  Q gatgtcacccagacgcttggccaacctggccagtcaagctgggtgaattgacacctagaggttgtgagctcattgcttacttgggtcac
D  V  T  P  D  A  W  P  T  W  P  V  K  L  G  E  L  T  P  R  G  C  E  L  I  A  Y  L  G  H tactggagacagcgtcttgttgccgacgaattgttgcctaagtgtggttgtccacaatctggtcaagtagctattattgctgacgtcgac
Y  W  R  Q  R  L  V  A  D  E  L  L  P  K  C  G  C  P  Q  S  G  Q  V  A  I  I  A  D  V  D gaaagaaccgtaagacaggtgaatgtttcgccgccggtcttgctcctgactgtgccattaccgttcaccatcaagctgacacttcttct
E  R  T  K  T  G  E  C  F  A  A  G  L  A  P  D  C  A  I  T  V  H  H  Q  A  D  T  S  S ccagatccattgttcaacccttgaagactggtgtttgccaattggacgttgctaacgttactagagctatcttggaagagctggagga
P  D  P  L  F  N  P  L  K  T  G  V  C  Q  L  D  V  A  N  V  T  R  A  I  L  E  E  L  E  D tctattgctgacttcaccggtcactaccagactgccttcagagagttggaaagagttcttaacttcccacaatccaacttgtgcttaag
S  I  A  D  F  T  G  H  Y  Q  T  A  F  R  E  L  E  R  V  L  N  F  P  Q  S  N  L  C  L  K cgtgagaagcaagacgaatcctgttcttgactcaagcattaccatctgagttgaaggtctccgccgacaacgtctctttgaccggtgct
R  E  K  Q  D  E  S  C  S  L  T  Q  A  L  P  S  E  L  K  V  S  A  D  D  V  S  L  T  G  A gtcagcttggcttccatgttgactgaaatcttcttctgcaacaagctcaaggtatgctgagccaggttggggtagaatcaccgactct
V  S  L  A  S  M  L  T  E  I  F  L  L  Q  Q  A  Q  G  M  P  E  P  G  W  G  R  I  T  D  S caccaatggaacaccttgttgtccttgcacaacgctcaattcgatttgctgcagagaactccagaggtt tgt agatccagagccaccca
H  Q  W  N  T  L  L  S  L  H  N  A  Q  F  D  L  L  Q  R  T  P  E  V  [C]  P  S  P  A  T  P ttgttggacttgatcaagactgcttgactcctcacccacctcaaaagcaagcctacggtgttacttgccacttctgtcttgttcatt
L  L  D  L  I  K  T  A  L  T  P  H  P  P  Q  K  Q  A  Y  G  V  T  L  P  T  S  V  L  F  I gccggtcacgatactaacttggcatgtctcggcggtgctttggagttgaactggactcttcctggtcaacctgataacactccaccaggt
A  G  H  D  T  N  L  A  [C]  L  G  G  A  L  E  L  N  W  T  L  P  G  Q  P  D  N  T  P  P  G ggtgagctcgttttcgaaagatggcgtagactatctgataactctcaatggattcaggtttcgttggtcttccaaactttgcagcagatg
G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
R  D  K  T  P  L  S  L  N  T  P  P  G  E  V  K  L  T  L  A  G  C  E  E  R  N  A  Q  G  M tgttccttggctggtttcactcaaatcgttaacgaagctagaatcccagcttgttccttgtagtaa  -SEQ ID NO. 29
C  S  L  A  G  F  T  Q  I  V  N  E  A  R  I  P  A  C  S  L  *  *    -SEQ ID NO. 30

FIG. 7

```
cagagtgagcctgagttgaaactggaatccgttgtcatcgtctctagacatggtgttagagcaccaaccaagttcacccaacttatgcaa
 Q  S  E  P  E  L  K  L  E  S  V  V  I  V  S  R  H  G  V  R  A  P  T  K  F  T  Q  L  M  Q gatgtcaccccagacgcttggccaacctggccagtcaagctgggtgaattgacacctagaggttgtgagctcattgcttacttgggtcac
 D  V  T  P  D  A  W  P  T  W  P  V  K  L  G  E  L  T  P  R  G  C  E  L  I  A  Y  L  G  H tactggagacagcgtcttgttgccgacgaattgttgcctaagtgtggttgtccacaatctggtcaagtagctattattgctgacgtcgac
 Y  W  R  Q  R  L  V  A  D  E  L  L  P  K  C  G  C  P  Q  S  G  Q  V  A  I  I  A  D  V  D gaaagaacccgtaagacaggtgaatgtttcgccgccggtcttgctcctgactgtgccattaccgttcaccatcaagctgacacttcttct
 E  R  T  R  K  T  G  E  C  F  A  A  G  L  A  P  D  C  A  I  T  V  H  H  Q  A  D  T  S  S ccagatccattgttcaaccctttgaagactggtgtttgccaattggacgttgctaacgttactagatgtatcttggaaagagctggagga
 P  D  P  L  F  N  P  L  K  T  G  V  C  Q  L  D  V  A  N  V  T  R  C  I  L  E  R  A  G  G tctattgctgacttcaccggtcactaccagactgccttcagagagttggaaagagttcttaacttcccacaatccaacttgtgccttaag
 S  I  A  D  F  T  G  H  Y  Q  T  A  F  R  E  L  E  R  V  L  N  F  P  Q  S  N  L  C  L  K cgtgagaagcaagacgaatcctgttccttgactcaagcattaccatctgagttgaaggtctccgccgacaacgtctctttgaccggtgct
 R  E  K  Q  D  E  S  C  S  L  T  Q  A  L  P  S  E  L  K  V  S  A  D  N  V  S  L  T  G  A gtcagcttggcttccatgttgactgaaatcttcttgcaacaagctcaaggtatgcctgagccaggttggggtagaatcaccgactct
 V  S  L  A  S  M  L  T  E  I  F  L  L  Q  Q  A  Q  G  M  P  E  P  G  W  G  R  I  T  D  S caccaatggaacaccttgttgtccttgcacaacgctcaattcgatttgctgcagtgtactccatgtgttgctagatccagagccacccca
 H  Q  W  N  T  L  L  S  L  H  N  A  Q  F  D  L  L  Q  C  T  P  C  V  A  R  S  R  A  T  P ttgttggacttgatcaagactgctttgactcctcacccacctcaaaagcaagcctacggtgttaccttgccacttctgtcttgttcatt
 L  L  D  L  I  K  T  A  L  T  P  R  P  P  Q  K  Q  A  Y  G  V  T  L  P  T  S  V  L  F  I gccggtcacgatactaacttggcaaatctcggdtgtgctttggagttgaactggactcttcctggtcaacctgataacactccaccaggt
 A  G  H  D  T  N  L  A  N  L  G  C  A  L  E  L  N  W  T  L  P  G  Q  P  D  N  T  P  P  G ggtgagctcgtttttcgaaagatggcgtagactatctgataactctcaatggattcagtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
 R  D  K  T  P  L  S  L  N  T  P  P  G  E  V  K  L  T  L  A  G  C  E  E  R  N  A  Q  G  M tgttccttggctggtttcactcaaatcgttaacgaagctagaatcccagcttgttccttgtagtaa    -SEQ ID NO. 31
 C  S  L  A  G  F  T  Q  I  V  N  E  A  R  I  P  A  C  S  L  *  *    -SEQ ID NO. 32
```

FIG. 8 cagagtgagcctgagttgaaactggaatccgttgtcatcgtctctagacatggtgttagagcaccaaccaagttcacccaacttatgcaa
 Q  S  E  F  E  L  K  L  E  S  V  V  I  V  S  R  H  G  V  R  A  P  T  K  F  T  Q  L  M  Q gatgtcaccccagacgcttggccaacctggccagtcaagctgggtgaattgacacctagaggttgtgagctcattgcttacttgggtcac
 D  V  T  P  D  A  W  P  T  W  P  V  K  L  G  E  L  T  P  R  G  C  E  L  I  A  Y  L  G  H tactggagacagcgtcttgttgccgacgaattgttgcctaagtgtggttgtccacaatctggtcaagtagctattattgctgacgtcgac
 Y  W  R  Q  R  L  V  A  D  E  L  L  P  K  C  G  C  P  Q  S  G  Q  V  A  I  I  A  D  V  D gaaagaaccgtaagacaggtgaatgtttcgccgccggtcttgctcctgactgtgccattaccgttcaccatcaagctgacacttcttct
 E  R  T  K  T  G  E  C  F  A  A  G  L  A  P  D  C  A  I  T  V  H  H  Q  A  D  T  S  S ccagatccattgttcaaccctttgaagactggtgtttgccaattggacgttgctaacgttactaga tgt atcttggaaagagctggagga
 P  D  P  L  F  N  P  L  K  T  G  V  C  Q  L  D  V  A  N  V  T  R  C  I  L  E  R  A  G  G tctattgctgacttcaccggtcactaccagactgccttcagagagttggaaagagttcttaacttcccacaatccaacttgtgccttaag
 S  I  A  D  F  T  G  H  Y  Q  T  A  F  R  E  L  E  R  V  L  N  F  P  Q  S  N  L  C  L  K cgtgagaagcaagacgaatcctgttccttgactcaagcattaccatctgagttgaaggtctccgccgacaacgtctctttgaccggtgct
 R  E  K  Q  D  E  S  C  S  L  T  Q  A  L  P  S  E  L  K  V  S  A  D  N  V  S  L  T  G  A gtcagcttggcttccatgttgactgaaatcttcttctgcaacaagctcaaggtatgctgagccaggttggggtagaatcaccgactct
 V  S  L  A  S  R  L  T  E  I  F  L  L  Q  Q  A  Q  G  S  R  P  E  P  G  W  G  R  I  T  D  S caccaatggaacaccttgttgtccttgcacaacgctcaattcgatttgctgcagagaactcc tgt ttg tgt agatccagagccacccca
 H  Q  W  N  T  L  L  S  L  H  N  A  Q  F  D  L  L  Q  R  T  P  C  V  C  R  S  R  A  T  P ttgttggacttgatcaagactgctttgactcctcacccacctcaaaagcaagcctacggtgttaccttgccacttctgtcttgttcatt
 L  L  D  L  I  K  T  A  L  T  P  H  P  P  Q  K  Q  A  Y  G  V  T  L  P  T  S  V  L  F  I gccggtcacgatactaacttggca tgt ctcggcggtgctttggagttgaactggactcttcctggtcaacctgataacactccaccaggt
 A  G  H  D  T  N  L  A  C  L  G  G  A  L  E  L  N  W  T  L  P  G  Q  P  D  N  T  P  P  G ggtgagctcgttttcgaaagatggcgtagactatctgataactctcaatggattcaggtttcgttggtcttccaaactttgcagcagatg
 G  E  L  V  F  E  R  W  R  R  L  S  D  N  S  Q  W  I  Q  V  S  L  V  F  Q  T  L  Q  Q  M agagacaagactccactgtctttgaacacgcctccaggagaagtcaaattgaccttggctggatgtgaagagagaaatgctcagggtatg
 R  D  K  T  P  L  S  L  N  T  P  P  G  E  V  K  L  T  L  A  G  C  E  E  R  N  A  Q  G  M tgttccttggctggtttcactcaaatcgttaacgaagctagaatcccagcttgttccttgtagtaa -SEQ ID NO. 33
 C  S  L  A  G  F  T  Q  I  V  N  E  A  R  I  P  A  C  S  L  *  *    -SEQ ID NO. 34

FIG. 9

PHYTASE HAVING IMPROVED THERMOSTABILITY

FIELD OF THE INVENTION

The present invention relates to a phytase, and more particularly to a phytase having improved thermostability.

BACKGROUND OF THE INVENTION

Phytic acid or phytate (myo-inositol hexakisphosphate) is the primary storage form of phosphorus in most plants and is abundant in seeds and legumes. However, the monogastric animals cannot utilize phosphorous from phytate due to the lack of necessary enzymes in digestive tract. Supplementation of inorganic phosphates is a solution used to compensate the shortage in phosphorus ingestion but the excessive phosphorus in animal excretion has caused environmental pollution. In addition, the insoluble complexes formed by the highly negatively charged phytate with proteins and metal ions are major anti-nutritional factors. Phytase can hydrolyze phytate to lower inositol phosphates to release inorganic phosphate and thus has been widely applied in animal feeds to increase phosphorus availability and reduce phosphorus pollution. To date, phytase is estimated to account for 60% of feed enzyme products for increasing nutrient absorption and also reducing 50% phosphorus excretion.

Classified by protein structure and catalytic property, there are four types of phytases including histidine acid phosphatases (HAPs), protein tyrosine phosphatase (PTP)-like phytases, purple acid phosphatases (PAPs) and β-propeller phytases (BPPs), with a majority of the characterized enzymes belonging to HAP. From previous studies, the crystal structures of all families except for PAP have been solved. Among the characterized phytases, *Escherichia coli* phytase (EcAppA), a member of the HAP family, has drawn much attention. First, EcAppA has high specific activity (up 56 to 2000 U/mg) under the favorable pH profile for feed additive. Second, large scale production of EcAppA in an industrial strain of *Pichia pastoris* has been successfully achieved by using fermentor for commercial applications. However, the need to enhance the thermostability of EcAppA still remains.

Molecular engineering is a powerful approach to modify enzyme performances. Directed evolution involving random mutagenesis which builds a library provides a large pool of mutants for subsequent screening for useful mutants. But the efficiency is low and the procedure is laborious. A more ideal way is rational design, which is realized by the increasing information of protein structure and the development of powerful bioinformatics tools. Major obstacle in conducting a successful rational design is how to choose the useful residues or structural features.

According to previous studies, thermostable proteins have more hydrogen bonds and salt bridges between side chains of amino acids. In addition, based on structure and characteristic analysis of mutated T4 lysozymes, it is observed that protein thermostability can be improved by increasing stability of hydrophobic center, enhancing hydrogen bonds and salt bridges, or adding disulfide bond. More and more studies use computer simulations to improve protein thermostability, and the mutated protein structures establish a set of parameters by computer analysis. These parameters can be used for narrowing the screening scope of mutation positions when improving thermostability of other target proteins.

Therefore, the present invention intends to add disulfide bond of phytase by gene modification, so as to improve thermostability and further increase industrial value of phytase.

SUMMARY OF THE INVENTION

An object of the present invention is to modify a phytase by means of structural analysis and site-directed mutagenesis for adding disulfide bond of the phytase, so as to efficiently improve thermostability and further increase industrial value of the phytase.

According to an aspect of the present invention, there is provided a phytase comprising a modified amino acid sequence of SEQ ID NO: 2, wherein the modification is one of mutations A to D. The mutation A is to substitute amino acids at positions 143 and 262 with cysteine, the mutation B is to substitute amino acids at positions 259 and 312 with cysteine, the mutation C is to substitute amino acids at positions 205 and 257 with cysteine, and the mutation D is to substitute amino acids at positions 264 and 309 with cysteine.

In an embodiment, a gene encoding the amino acid sequence of SEQ ID NO: 2 is isolated from *Escherichia coli* and optimized.

In an embodiment, the phytase is a histidine acid phosphatase.

In an embodiment, the phytase has a full length amino acid sequence of SEQ ID NO: 24.

In an embodiment, the phytase has a full length amino acid sequence of SEQ ID NO: 26.

In an embodiment, the phytase has a full length amino acid sequence of SEQ ID NO: 28.

In an embodiment, the phytase has a full length amino acid sequence of SEQ ID NO: 30.

According to another aspect of the present invention, there is provided a phytase comprising a modified amino acid sequence of SEQ ID NO: 2, wherein the modification combines mutation A and one of mutations B and D. The mutation A is to substitute amino acids at positions 143 and 262 with cysteine, the mutation B is to substitute amino acids at positions 259 and 312 with cysteine, and the mutation D is to substitute amino acids at positions 264 and 309 with cysteine.

In an embodiment, a gene encoding the amino acid sequence of SEQ ID NO: 2 is isolated from *Escherichia coli* and optimized.

In an embodiment, the phytase is a histidine acid phosphatase.

In an embodiment, the phytase has a full length amino acid sequence of SEQ ID NO: 32.

In an embodiment, the phytase has a full length amino acid sequence of SEQ ID NO: 34.

The above objects and advantages of the present invention will become more readily apparent to those ordinarily skilled in the art after reviewing the following detailed description and accompanying drawings, in which:

BRIEF DESCRIPTION OF THE DRAWINGS

FIG. 1 shows the nucleotide sequence and the amino acid sequence of the wild type AppA;

FIG. 3 shows the mutagenic primers for site-directed mutagenesis;

FIG. 4 shows the nucleotide sequence and the amino acid sequence of the mutant AppA-A;

FIG. 5 shows the nucleotide sequence and the amino acid sequence of the mutant AppA-B;

FIG. 6 shows the nucleotide sequence and the amino acid sequence of the mutant AppA-C;

FIG. 7 shows the nucleotide sequence and the amino acid sequence of the mutant AppA-D;

FIG. 8 shows the nucleotide sequence and the amino acid sequence of the mutant AppA-A+B;

FIG. 9 shows the nucleotide sequence and the amino acid sequence of the mutant AppA-A+D.

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

In the present invention, the gene of the phytase EcAppA is isolated from *Escherichia coli*, and EcAppA is a histidine acid phosphatase (HAP). EcAppA has high enzymatic activity, high substrate specificity, favorable pH profile, and high expression in industrial strain of *Pichia pastoris*, and thus possesses high industrial value. To increase the enzymatic activity of EcAppA after feed pelleting, the thermostability of EcAppA needs to be improved for further increasing the industrial value of EcAppA. Since the protein structure of EcAppA has been solved, EcAppA is a favorable target for enzyme modification.

Due to disulfide bond addition, the protein stability is increased and the irreversible structure extension of protein resulted from high temperature is reduced, and thus the thermostability of EcAppA is successfully improved in the present invention. The position for the added disulfide bond is the key point for the technique, and the present invention utilizes rational design to select mutation positions for disulfide bond addition so as to further improve the thermostability of EcAppA. Based on the premise of not affecting the whole protein structure after the disulfide bond is formed, the mutation positions for disulfide bond addition are selected to locate at where the protein structure is close in space, and are screened by parameters for the distance between β-carbon atoms in side chains of amino acids of 4.0 Å, 4.5 Å, 5.0 Å, and 5.5 Å. Adding the disulfide bond on the surface of the stabler protein secondary structure is beneficial to increase the protein stability. After eliminating ineffective disulfide bonds at turns of the original protein secondary structure, the remaining mutations are further screened by thermostability analysis.

The enzyme modification processes and the resulted phytase proteins are described in detail as follows.

The present invention utilizes site-directed mutagenesis for enzyme modification, and employs the industrial strain of *Pichia pastoris* for protein expression. First, the EcAppA gene is optimized as AppA which is easy to be expressed in *Pichia pastoris*. FIG. 1 shows the nucleotide sequence and the amino acid sequence of the wild type AppA, wherein the wild type AppA gene consists of 1236 base pairs (SEQ ID NO: 1, including the stop codon) and encodes 410 amino acids (SEQ ID NO: 2). The AppA gene is constructed into pPICZαA vector by using EcoRI and NotI sites, and then the site-directed mutagenesis is performed.

Figure 2:
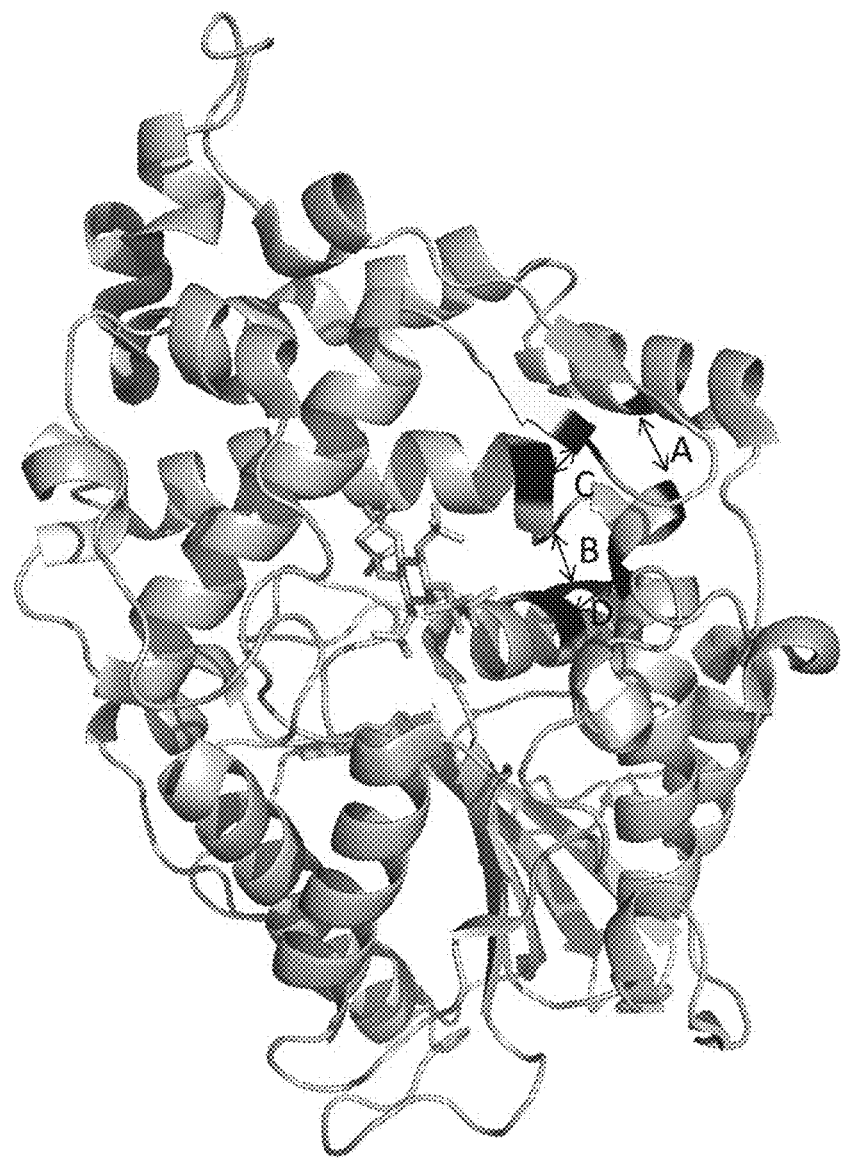
FIG. 2 shows the protein structure of the wild-type AppA and the mutation positions.

FIG. 2 shows the protein structure of the wild-type AppA and the mutation positions. The structures of AppA protein (PDB: 1DKQ) and inositol hexaphosphate are illustrated with grey color, and the positions of the mutations A (143-262), B (259-312), C (205-257) and D (264-309) for disulfide bond addition are illustrated with black color. As described above, the mutation positions at the surface of the protein secondary structure are screened by parameters for the distance between β-carbon atoms in side chains of amino acids of 4.0 Å, 4.5 Å, 5.0 Å, and 5.5 Å, and the mutation positions at turns of the protein secondary structure are eliminated. As a result, the mutants AppA-A, AppA-B, AppA-C and AppA-D are selected, wherein the mutant AppA-A includes the mutation A which is to substitute the amino acids at positions 143 and 262 with cysteine, the mutant AppA-B includes the mutation B which is to substitute the amino acids at positions 259 and 312 with cysteine, the mutant AppA-C includes the mutation C which is to substitute the amino acids at positions 205 and 257 with cysteine, and the mutant AppA-D includes the mutation D which is to substitute the amino acids at positions 264 and 309 with cysteine. The distances between β-carbon atoms in side chains of amino acids for the mutants AppA-A, AppA-B, AppA-C and AppA-D are 4.0 Å, 4.1 Å, 5.1 Å, and 4.3 Å, respectively, wherein since the amino acid at position 312 is glycine having no side chain, the distance of 4.1 Å is the distance between the α-carbon atom of glycine and the β-carbon atom in the side chain of the amino acid at position 259.

The mutagenic primers for site-directed mutagenesis are shown in FIG. 3. The sequences of the primers are numbered as SEQ ID NOS: 3 to 22, wherein F means the forward primer, R means the reverse primer, and the mutation positions are underlined. The mutations for the mutants AppA-A, AppA-B, AppA-C and AppA-D are A (143-262), B (259-312), C (205-257) and D (264-309), respectively. A1 and A2 mean the primers used for mutations at position 143 and position 262, respectively, in the mutation A (143-262). B1 and B2 mean the primers used for mutations at position 259 and position 312, respectively, in the mutation B (259-312). C1 and C2 mean the primers used for mutations at position 205 and position 257, respectively, in the mutation C (205-257). D1 and D2 mean the primers used for mutations at position 264 and position 309, respectively, in the mutation D (264-309). In addition, the present invention further performs a modification including the mutations A+B (143-262 and 259-312) to obtain a mutant AppA-A+B, and a modification including the mutations A+D (143-262 and 264-309) to obtain a mutant AppA-A+D. The mutagenic primers used for AppA-A+B include three primer pairs of A1, A2+B1 and B2, and the mutagenic primers used for AppA-A+D include three primer pairs of A1, A2+D1 and D2.

Site-directed mutagenesis is to use the mutagenic primers for polymerase chain reaction (PCR). The original templates are removed via DpnI digestion under 37° C., and then the plasmids with the mutated genes are transformed into *E. coli* XL1B competent cells. The transformants are cultured on LB plates containing 50 μg/ml Zeocin at 37° C. for 1 day. Finally, the mutated genes of the picked colonies are confirmed by DNA sequencing.

FIG. 4 shows the nucleotide sequence and the amino acid sequence of the mutant AppA-A, wherein the mutant AppA-A gene consists of 1236 base pairs (SEQ ID NO: 23, including the stop codon) and encodes 410 amino acids (SEQ ID NO: 24). The amino acids at position 143 and position 262 are both mutated into cysteine.

FIG. 5 shows the nucleotide sequence and the amino acid sequence of the mutant AppA-B, wherein the mutant AppA-B gene consists of 1236 base pairs (SEQ ID NO: 25, including the stop codon) and encodes 410 amino acids (SEQ ID NO: 26). The amino acids at position 259 and position 312 are both mutated into cysteine.

FIG. 6 shows the nucleotide sequence and the amino acid sequence of the mutant AppA-C, wherein the mutant AppA-C gene consists of 1236 base pairs (SEQ ID NO: 27, including the stop codon) and encodes 410 amino acids (SEQ ID NO: 28). The amino acids at position 205 and position 257 are both mutated into cysteine.

FIG. 7 shows the nucleotide sequence and the amino acid sequence of the mutant AppA-D, wherein the mutant AppA-D gene consists of 1236 base pairs (SEQ ID NO: 29, including the stop codon) and encodes 410 amino acids (SEQ ID NO: 30). The amino acids at position 264 and position 309 are both mutated into cysteine.

FIG. 8 shows the nucleotide sequence and the amino acid sequence of the mutant AppA-A+B, wherein the mutant AppA-A+B gene consists of 1236 base pairs (SEQ ID NO: 31, including the stop codon) and encodes 410 amino acids (SEQ ID NO: 32). The amino acids at position 143, position 259, position 262 and position 312 are all mutated into cysteine.

FIG. 9 shows the nucleotide sequence and the amino acid sequence of the mutant AppA-A+D, wherein the mutant AppA-A+D gene consists of 1236 base pairs (SEQ ID NO: 33, including the stop codon) and encodes 410 amino acids (SEQ ID NO: 34). The amino acids at position 143, position 262, position 264 and position 309 are all mutated into cysteine.

The modified DNA plasmids are linearized by PmeI and then transformed into *Pichia pastoris* by electroporation. The transformants are selected on YPD plates containing 100 μg/ml Zeocin and cultured at 30° C. for 2 days. The picked colonies are inoculated in 1 ml of YPD at 30° C. for 1 day, and the medium in a volume with 0.2 of OD600 is further amplified in 5 ml of BMGY at 30° C. for 24 hr. The cells are harvested and then resuspended in 2 ml of BMMY containing 0.5% methanol to induce protein expression at 30° C. for 2-3 days. The cells are harvested by centrifugation and the supernatant is collected, and the activity and the thermostability of the phytase are further analyzed.

Phytase activity is measured as follows. First, 4 ml of 7.5 mM sodium phytate, 0.2 ml of enzyme protein (in buffer of 0.05% Triton X-100, 0.05% BSA and 0.25 M sodium acetate, pH5.5) and 1.8 ml of 0.25 M sodium acetate (pH 5.5) are incubated at 37° C. for 30 min. The reaction is stopped by adding 4 ml of stop reagent (water: nitric acid: 10% ammonium molybdate: 0.2 M ammonium vanadate=4:2:1:1). OD415 is measured and then converted into enzyme activity unit. The standard curve of the enzyme activity is determined by 0-25 μmol/ml standard solution of potassium dihydrogen phosphate. One unit of phytase activity is defined as the amount of enzyme required to liberate 1 μmol of inorganic phosphate from 5 mM sodium phytate per minute.

For the thermostability analysis, the supernatants of the wild type and all mutant proteins are diluted into same activity and then tested on the PCR machine. The samples are heat-treated at 85° C. for 2 min and subsequently cooled at 25° C. The activities of the proteins without heat treatment are set to 100% and the relative residual activities of the heat-treated proteins are determined.

Figure 10:
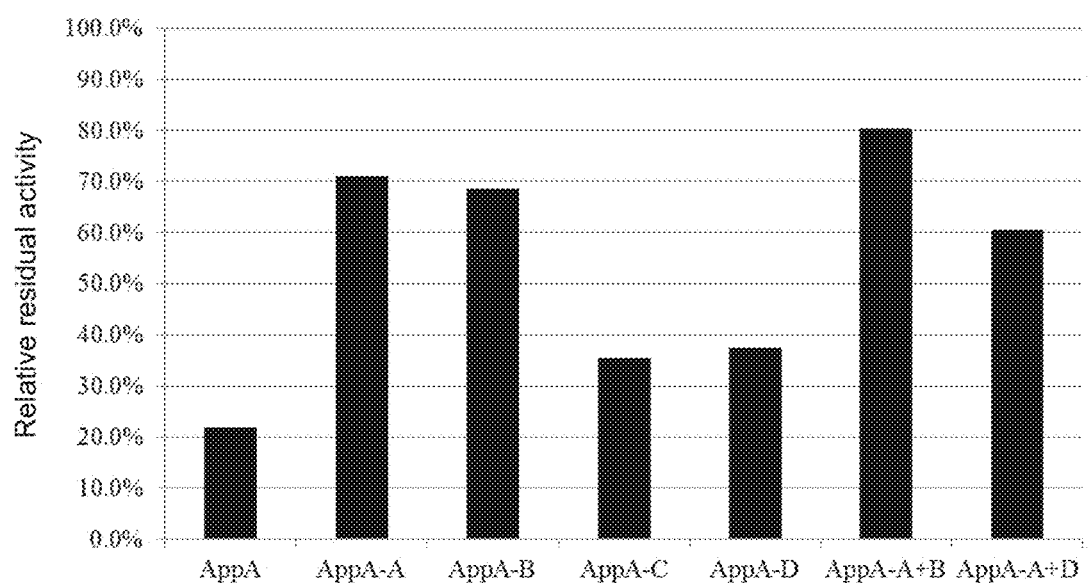
FIG. 10 shows the thermostability analysis of the wild type phytase AppA and the mutant AppA with different mutations.

FIG. 10 shows the thermostability analysis of the wild type phytase AppA and the mutant AppA with different mutations. From FIG. 10, it is observed that after heat-treated at 85° C. for 2 min, the relative residual activity of the wild type AppA is 21.7%, while the relative residual activities of the mutants AppA-A, AppA-B, AppA-C and AppA-D are 70.9%, 68.5%, 35.4% and 37.4%, respectively, which are all higher than the wild type AppA. Further, the relative residual activities of the mutants AppA-A+B and AppA-A+D are 80.5% and 60.6%, respectively, which are also higher than the wild type AppA. In other words, the structure of the phytase AppA is stabilized by adding disulfide bonds, so that the relative residual activities of the mutants AppA-A, AppA-B, AppA-C, AppA-D, AppA-A+B and AppA-A+D are all higher than the wild type AppA after heat-treated at 85° C. for 2 min. Therefore, the modified phytases provided in the present invention have improved thermostability, can increase the thermostability in pelleting process and reduce the production cost, and thus have higher industrial value.

In conclusion, to further increase the industrial value of the phytase, the present invention utilizes rational design to select mutation positions for disulfide bond addition, so as to increase the protein stability and further improve the thermostability of the phytase. The present invention selects four mutations, wherein the mutant AppA-A adds a disulfide bond between the amino acid at position 143 and the amino acid at position 262, the mutant AppA-B adds a disulfide bond between the amino acid at position 259 and the amino acid at position 312, the mutant AppA-C adds a disulfide bond between the amino acid at position 205 and the amino acid at position 257, and the mutant AppA-D adds a disulfide bond between the amino acid at position 264 and the amino acid at position 309. The present invention further combines the mutations, and the combined modifications include AppA-A+B and AppA-A+D. According to the thermostability analysis, the relative residual activities of the mutants AppA-A, AppA-B, AppA-C, AppA-D, AppA-A+B and AppA-A+D are all higher than the wild type AppA after heat-treated at 85° C. for 2 min. Therefore, the modified phytases provided in the present invention have improved thermostability. In other words, the screening technique for disulfide bond addition provided in the present invention effectively targets the mutations that can improve the thermostability of the protein and effectively increases the screening efficiency. The selected mutations all significantly improve the thermostability of the phytase, can increase the thermostability in pelleting process and reduce the production cost, and thus have higher industrial value.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A phytase consisting of a modified amino acid sequence of SEQ ID NO: 2, wherein the modification is one of mutations A to D, the mutation A is to substitute amino acids at positions 143 and 262 with cysteine, the mutation B is to substitute amino acids at positions 259 and 312 with cysteine, the mutation C is to substitute amino acids at positions 205 and 257 with cysteine, and the mutation D is to substitute amino acids at positions 264 and 309 with cysteine.

2. The phytase according to claim 1 wherein the amino acid sequence of SEQ ID NO: 2 is encoded by the nucleic acid sequence of SEQ ID NO: 1.

3. The phytase according to claim 1 being a histidine acid phosphatase.

4. The phytase according to claim 1 having the full length amino acid sequence of SEQ ID NO: 24.

5. The phytase according to claim 1 having the full length amino acid sequence of SEQ ID NO: 26.

6. The phytase according to claim 1 having the full length amino acid sequence of SEQ ID NO: 28.

7. The phytase according to claim 1 having the full length amino acid sequence of SEQ ID NO: 30.

8. A phytase consisting of a modified amino acid sequence of SEQ ID NO: 2, wherein the modification combines mutation A and one of mutations B and D, the mutation A is to substitute amino acids at positions 143 and 262 with cysteine, the mutation B is to substitute amino acids at positions 259 and 312 with cysteine, and the mutation D is to substitute amino acids at positions 264 and 309 with cysteine.

9. The phytase according to claim 8 wherein the amino acid sequence of SEQ ID NO: 2 is encoded by the nucleic acid sequence of SEQ ID NO: 1.

10. The phytase according to claim 8 being a histidine acid phosphatase.

11. The phytase according to claim 8 having the full length amino acid sequence of SEQ ID NO: 32.

12. The phytase according to claim 8 having the full length amino acid sequence of SEQ ID NO: 34.

* * * * *

SEQUENCE LISTING

<160> NUMBER OF SEQ ID NOS: 34

<210> SEQ ID NO 1
<211> LENGTH: 1236
<212> TYPE: DNA
<213> ORGANISM: Escherichia coli

<400> SEQUENCE: 1

| | | |
|---|---|---|
| cagagtgagc ctgagttgaa actggaatcc gttgtcatcg tctctagaca tggtgttaga | 60 |
| gcaccaacca agttcaccca acttatgcaa gatgtcaccc agacgcttg gccaacctgg | 120 |
| ccagtcaagc tgggtgaatt gacacctaga ggttgtgagc tcattgctta cttgggtcac | 180 |
| tactggagac agcgtcttgt tgccgacgaa ttgttgccta agtgtggttg tccacaatct | 240 |
| ggtcaagtag ctattattgc tgacgtcgac gaaagaaccc gtaagacagg tgaatgtttc | 300 |
| gccgccggtc ttgctcctga ctgtgccatt accgttcacc atcaagctga cacttcttct | 360 |
| ccagatccat tgttcaaccc tttgaagact ggtgtttgcc aattggacgt tgctaacgtt | 420 |
| actagagcta tcttggaaag agctggagga tctattgctg acttcaccgg tcactaccag | 480 |
| actgccttca gagagttgga aagagttctt aacttcccac aatccaactt gtgccttaag | 540 |
| cgtgagaagc aagacgaatc ctgttccttg actcaagcat accatctga gttgaaggtc | 600 |
| tccgccgaca acgtctcttt gaccggtgct gtcagcttgg cttccatgtt gactgaaatc | 660 |
| tttcttctgc aacaagctca aggtatgcct gagccaggtt ggggtagaat caccgactct | 720 |
| caccaatgga acaccttgtt gtccttgcac aacgctcaat tcgatttgct gcagagaact | 780 |
| ccagaggttg ctagatccag agccacccca ttgttggact tgatcaagac tgctttgact | 840 |
| cctcacccac tcaaaagca agcctacggt gttaccttgc ccacttctgt cttgttcatt | 900 |
| gccggtcacg atactaactt ggcaaatctc ggcggtgctt tggagttgaa ctggactctt | 960 |
| cctggtcaac tgataacac tccaccaggt ggtgagctcg ttttcgaaag atggcgtaga | 1020 |
| ctatctgata actctcaatg gattcaggtt tcgttggtct tccaaacttt gcagcagatg | 1080 |
| agagacaaga ctccactgtc tttgaacacg cctccaggag aagtcaaatt gaccttggct | 1140 |
| ggatgtgaag agagaaatgc tcagggtatg tgttccttgg ctggtttcac tcaaatcgtt | 1200 |
| aacgaagcta gaatcccagc ttgttccttg tagtaa | 1236 |

<210> SEQ ID NO 2
<211> LENGTH: 410
<212> TYPE: PRT
<213> ORGANISM: Escherichia coli

<400> SEQUENCE: 2

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Cys Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

-continued

Gly Glu Cys Phe Ala Ala Gly Leu Ala Pro Asp Cys Ala Ile Thr Val
                100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 3
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 3
gctaacgtta ctagatgtat cttggaaaga gct                                33

<210> SEQ ID NO 4
<211> LENGTH: 33
<212> TYPE: DNA
<213> ORGANISM: Artificial Sequence
<220> FEATURE:
<223> OTHER INFORMATION: Synthetically generated primer

```
<400> SEQUENCE: 4
agctctttcc aagatacatc tagtaacgtt agc                                    33

<210> SEQ ID NO 5
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 5
ctgcagagaa ctccatgtgt tgctagatcc aga                                    33

<210> SEQ ID NO 6
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 6
tctggatcta gcaacacatg gagttctctg cag                                    33

<210> SEQ ID NO 7
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 7
ttcgatttgc tgcagtgtac tccagaggtt gct                                    33

<210> SEQ ID NO 8
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 8
agcaacctct ggagtacact gcagcaaatc gaa                                    33

<210> SEQ ID NO 9
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 9
ttggcaaatc tcggctgtgc tttggagttg aac                                    33

<210> SEQ ID NO 10
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 10
gttcaactcc aaagcacagc cgagatttgc caa                                    33
```

```
<210> SEQ ID NO 11
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 11
gtctccgccg acaactgttc tttgaccggt gct                              33

<210> SEQ ID NO 12
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 12
agcaccggtc aaagaacagt tgtcggcgga gac                              33

<210> SEQ ID NO 13
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 13
gctcaattcg atttgtgtca gagaactcca gag                              33

<210> SEQ ID NO 14
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 14
ctctggagtt ctctgacaca aatcgaattg agc                              33

<210> SEQ ID NO 15
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 15
agaactccag aggtttgtag atccagagcc acc                              33

<210> SEQ ID NO 16
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 16
ggtggctctg gatctacaaa cctctggagt tct                              33

<210> SEQ ID NO 17
<211> LENGTH: 33
<212> TYPE: DNA
<213> ORGANISM: Artificial Sequence
<220> FEATURE:
<223> OTHER INFORMATION: Synthetically generated primer
```

```
<400> SEQUENCE: 17
gatactaact tggcatgtct cggcggtgct ttg                                    33

<210> SEQ ID NO 18
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 18
caaagcaccg ccgagacatg ccaagttagt atc                                    33

<210> SEQ ID NO 19
<211> LENGTH: 42
<212> TYPE: DNA
<213> ORGANISM: Artificial Sequence
<220> FEATURE:
<223> OTHER INFORMATION: Synthetically generated primer

<400> SEQUENCE: 19
ttcgatttgc tgcagtgtac tccatgtgtt gctagatcca ga                          42

<210> SEQ ID NO 20
<211> LENGTH: 42
<212> TYPE: DNA
<213> ORGANISM: Artificial Sequence
<220> FEATURE:
<223> OTHER INFORMATION: Synthetically generated primer

<400> SEQUENCE: 20
tctggatcta gcaacacatg gagtacactg cagcaaatcg aa                          42

<210> SEQ ID NO 21
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 21
ctgcagagaa ctccatgtgt ttgtagatcc agagccacc                              39

<210> SEQ ID NO 22
<211> LENGTH: 39
<212> TYPE: DNA
<213> ORGANISM: Artificial Sequence
<220> FEATURE:
<223> OTHER INFORMATION: Synthetically generated primer

<400> SEQUENCE: 22
ggtggctctg gatctacaaa cacatggagt tctctgcag                              39

<210> SEQ ID NO 23
<211> LENGTH: 1236
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 23
cagagtgagc ctgagttgaa actggaatcc gttgtcatcg tctctagaca tggtgttaga       60
gcaccaacca agttcaccca acttatgcaa gatgtcaccc cagacgcttg gccaacctgg      120
```

```
ccagtcaagc tgggtgaatt gacacctaga ggttgtgagc tcattgctta cttgggtcac      180
tactggagac agcgtcttgt tgccgacgaa ttgttgccta agtgtggttg tccacaatct      240
ggtcaagtag ctattattgc tgacgtcgac gaaagaaccc gtaagacagg tgaatgtttc      300
gccgccggtc ttgctcctga ctgtgccatt accgttcacc atcaagctga cacttcttct      360
ccagatccat tgttcaaccc tttgaagact ggtgtttgcc aattggacgt tgctaacgtt      420
actagatgta tcttggaaag agctggagga tctattgctg acttcaccgg tcactaccag      480
actgccttca gagagttgga aagagttctt aacttcccac aatccaactt gtgccttaag      540
cgtgagaagc aagacgaatc ctgttccttg actcaagcat accatctga gttgaaggtc       600 tccgccgaca acgtctcttt gaccggtgct gtcagcttgg cttccatgtt gactgaaatc      660
tttcttctgc aacaagctca aggtatgcct gagccaggtt ggggtagaat caccgactct      720
caccaatgga acaccttgtt gtccttgcac aacgctcaat tcgatttgct gcagagaact      780
ccatgtgttg ctagatccag agccacccca ttgttggact tgatcaagac tgctttgact      840
cctcacccac ctcaaaagca agcctacggt gttaccttgc ccacttctgt cttgttcatt      900
gccggtcacg atactaactt ggcaaatctc ggcggtgctt tggagttgaa ctggactctt      960
cctggtcaac ctgataacac tccaccaggt ggtgagctcg ttttcgaaag atggcgtaga     1020
ctatctgata actctcaatg gattcaggtt tcgttggtct tccaaacttt gcagcagatg     1080
agagacaaga ctccactgtc tttgaacacg cctccaggag aagtcaaatt gaccttggct     1140
ggatgtgaag agagaaatgc tcagggtatg tgttccttgg ctggtttcac tcaaatcgtt     1200
aacgaagcta gaatcccagc ttgttccttg tagtaa                               1236
```

<210> SEQ ID NO 24
<211> LENGTH: 410
<212> TYPE: PRT
<213> ORGANISM: Artificial Sequence
<220> FEATURE:
<223> OTHER INFORMATION: Sequence synthetically translated from SEQ ID NO: 23

<400> SEQUENCE: 24

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Cys Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Cys Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Cys Ile
    130                 135                 140

Leu Glu Arg Ala Gly Gly Ser Ile Ala Asp Phe Thr Gly His Tyr Gln
145                 150                 155                 160
```

Thr Ala Phe Arg Glu Leu Glu Arg Val Leu Asn Phe Pro Gln Ser Asn
            165                 170                 175
Leu Cys Leu Lys Arg Glu Lys Gln Asp Glu Ser Cys Ser Leu Thr Gln
        180                 185                 190
Ala Leu Pro Ser Glu Leu Lys Val Ser Ala Asp Asn Val Ser Leu Thr
        195                 200                 205
Gly Ala Val Ser Leu Ala Ser Met Leu Thr Glu Ile Phe Leu Leu Gln
    210                 215                 220
Gln Ala Gln Gly Met Pro Glu Pro Gly Trp Gly Arg Ile Thr Asp Ser
225                 230                 235                 240
His Gln Trp Asn Thr Leu Leu Ser Leu His Asn Ala Gln Phe Asp Leu
                245                 250                 255
Leu Gln Arg Thr Pro Cys Val Ala Arg Ser Arg Ala Thr Pro Leu Leu
            260                 265                 270
Asp Leu Ile Lys Thr Ala Leu Thr Pro His Pro Pro Gln Lys Gln Ala
        275                 280                 285
Tyr Gly Val Thr Leu Pro Thr Ser Val Leu Phe Ile Ala Gly His Asp
    290                 295                 300
Thr Asn Leu Ala Asn Leu Gly Gly Ala Leu Glu Leu Asn Trp Thr Leu
305                 310                 315                 320
Pro Gly Gln Pro Asp Asn Thr Pro Pro Gly Gly Glu Leu Val Phe Glu
                325                 330                 335
Arg Trp Arg Arg Leu Ser Asp Asn Ser Gln Trp Ile Gln Val Ser Leu
            340                 345                 350
Val Phe Gln Thr Leu Gln Gln Met Arg Asp Lys Thr Pro Leu Ser Leu
        355                 360                 365
Asn Thr Pro Pro Gly Glu Val Lys Leu Thr Leu Ala Gly Cys Glu Glu
    370                 375                 380
Arg Asn Ala Gln Gly Met Cys Ser Leu Ala Gly Phe Thr Gln Ile Val
385                 390                 395                 400
Asn Glu Ala Arg Ile Pro Ala Cys Ser Leu
                405                 410

<210> SEQ ID NO 25
<211> LENGTH: 1236
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 25
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggttgtgagc tcattgctta cttgggtcac     180
tactggagac agcgtcttgt tgccgacgaa ttgttgccta gtgtggttg tccacaatct      240 ggtcaagtag ctattattgc tgacgtcgac gaaagaaccc gtaagacagg tgaatgtttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat taccatctga gttgaaggtc     600

```
tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga acaccttgtt gtccttgcac aacgctcaat tcgatttgct gcagtgtact    780
ccagaggttg ctagatccag agccaccca ttgttggact tgatcaagac tgctttgact     840
cctcacccac ctcaaaagca agcctacggt gttaccttgc ccacttctgt cttgttcatt    900
gccggtcacg atactaactt ggcaaatctc ggctgtgctt tggagttgaa ctggactctt    960
cctggtcaac tgataacac tccaccaggt ggtgagctcg ttttcgaaag atggcgtaga    1020
ctatctgata actctcaatg gattcaggtt tcgttggtct tccaaacttt gcagcagatg   1080
agagacaaga ctccactgtc tttgaacacg cctccaggag aagtcaaatt gaccttggct   1140
ggatgtgaag agagaaatgc tcagggtatg tgttccttgg ctggtttcac tcaaatcgtt   1200
aacgaagcta gaatcccagc ttgttccttg tagtaa                              1236
```

<210> SEQ ID NO 26
<211> LENGTH: 410
<212> TYPE: PRT
<213> ORGANISM: Artificial Sequence
<220> FEATURE:
<223> OTHER INFORMATION: Sequence synthetically translated from SEQ ID
     NO: 25

<400> SEQUENCE: 26

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Cys Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Cys Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240
```

His Gln Trp Asn Thr Leu Leu Ser Leu His Asn Ala Gln Phe Asp Leu
                245                 250                 255

Leu Gln Cys Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Cys Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 27
<211> LENGTH: 1236
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 27
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggttgtgagc tcattgctta cttgggtcac     180
tactggagac agcgtcttgt tgccgacgaa ttgttgccta agtgtggttg tccacaatct     240
ggtcaagtag ctattattgc tgacgtcgac gaaagaaccc gtaagacagg tgaatgtttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat accatctga gttgaaggtc      600 tccgccgaca ctgttctttt gaccggtgct gtcagcttgg cttccatgtt gactgaaatc     660
tttcttctgc aacaagctca aggtatgcct gagccaggtt ggggtagaat caccgactct     720
caccaatgga cacccttgtt gtccttgcac aacgctcaat tcgatttgtg tcagagaact     780
ccagaggttg ctagatccag agccaccca ttgttggact tgatcaagac tgctttgact      840
cctcacccac ctcaaaagca agcctacggt gttaccttgc ccacttctgt cttgttcatt     900
gccggtcacg atactaactt ggcaaatctc ggcggtgctt tggagttgaa ctggactctt     960
cctggtcaac tgataacac tccaccaggt ggtgagctcg ttttcgaaag atggcgtaga     1020
ctatctgata actctcaatg gattcaggtt cgttggtct tccaaacttt gcagcagatg     1080

-continued

```
agagacaaga ctccactgtc tttgaacacg cctccaggag aagtcaaatt gaccttggct    1140
ggatgtgaag agagaaatgc tcagggtatg tgttccttgg ctggtttcac tcaaatcgtt    1200
aacgaagcta gaatcccagc ttgttccttg tagtaa                              1236
```

<210> SEQ ID NO 28
<211> LENGTH: 410
<212> TYPE: PRT
<213> ORGANISM: Artificial Sequence
<220> FEATURE:
<223> OTHER INFORMATION: Sequence synthetically translated from SEQ ID
      NO: 27

<400> SEQUENCE: 28

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Cys Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Cys Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Cys Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Cys Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335
```

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 29
<211> LENGTH: 1236
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 29
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggttgtgagc tcattgctta cttgggtcac     180
tactggagac agcgtcttgt tgccgacgaa ttgttgccta gtgtggttg tccacaatct     240 ggtcaagtag ctattattgc tgacgtcgac gaaagaaccc gtaagacagg tgaatgtttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagagcta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat taccatctga gttgaaggtc     600
tccgccgaca cgtctctttt gaccggtgct gtcagcttgg cttccatgtt gactgaaatc     660
tttcttctgc aacaagctca aggtatgcct gagccaggtt ggggtagaat caccgactct     720
caccaatgga cacccttgtt gtccttgcac aacgctcaat tcgatttgct gcagagaact     780
ccagaggttt gtagatccag agccaccccca ttgttggact tgatcaagac tgcttttgact    840 cctcacccac ctcaaaagca agcctacggt gttaccttgc ccacttctgt cttgttcatt     900
gccggtcacg atactaactt ggcatgtctc ggcggtgctt tggagttgaa ctggactctt     960
cctggtcaac tgataacac tccaccaggt ggtgagctcg ttttcgaaag atggcgtaga    1020
ctatctgata actctcaatg gattcaggtt cgttggtct tccaaacttt gcagcagatg   1080
agagacaaga ctccactgtc tttgaacacg cctccaggag aagtcaaatt gaccttggct    1140
ggatgtgaag agagaaatgc tcagggtatg tgttccttgg ctggtttcac tcaaatcgtt    1200
aacgaagcta gaatcccagc ttgttccttg tagtaa                             1236

<210> SEQ ID NO 30
<211> LENGTH: 410
<212> TYPE: PRT
<213> ORGANISM: Artificial Sequence
<220> FEATURE:
<223> OTHER INFORMATION: Sequence synthetically translated from SEQ ID
      NO: 29

<400> SEQUENCE: 30

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Cys Glu Leu Ile Ala Tyr Leu Gly His Tyr Trp Arg Gln
    50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Cys Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Ala Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Cys Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Cys Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```

<210> SEQ ID NO 31
<211> LENGTH: 1236
<212> TYPE: DNA
<213> ORGANISM: Artificial Sequence
<220> FEATURE:
<223> OTHER INFORMATION: Synthetically generated DNA encoding a modified enzyme

<400> SEQUENCE: 31

```
cagagtgagc ctgagttgaa actggaatcc gttgtcatcg tctctagaca tggtgttaga      60
gcaccaacca agttcaccca acttatgcaa gatgtcaccc agacgcttg gccaacctgg      120
ccagtcaagc tgggtgaatt gacacctaga ggttgtgagc tcattgctta cttgggtcac     180
tactggagac agcgtcttgt tgccgacgaa ttgttgccta agtgtggttg tccacaatct     240
ggtcaagtag ctattattgc tgacgtcgac gaaagaaccc gtaagacagg tgaatgtttc     300
gccgccggtc ttgctcctga ctgtgccatt accgttcacc atcaagctga cacttcttct     360
ccagatccat tgttcaaccc tttgaagact ggtgtttgcc aattggacgt tgctaacgtt     420
actagatgta tcttggaaag agctggagga tctattgctg acttcaccgg tcactaccag     480
actgccttca gagagttgga aagagttctt aacttcccac aatccaactt gtgccttaag     540
cgtgagaagc aagacgaatc ctgttccttg actcaagcat accatctga ttgaaggtc      600
tccgccgaca acgtctcttt gaccggtgct gtcagcttgg cttccatgtt gactgaaatc     660
tttcttctgc aacaagctca aggtatgcct gagccaggtt ggggtagaat caccgactct     720
caccaatgga acaccttgtt gtccttgcac aacgctcaat tcgatttgct gcagtgtact     780
ccatgtgttg ctagatccag agccacccca ttgttggact tgatcaagac tgctttgact     840
cctcacccac tcaaaagca agcctacggt gttaccttgc ccacttctgt cttgttcatt     900
gccggtcacg atactaactt ggcaaatctc ggctgtgctt tggagttgaa ctggactctt     960
cctggtcaac tgataacac tccaccaggt ggtgagctcg ttttcgaaag atggcgtaga    1020
ctatctgata actctcaatg gattcaggtt tcgttggtct tccaaacttt gcagcagatg    1080
agagacaaga ctccactgtc tttgaacacg cctccaggag aagtcaaatt gaccttggct    1140
ggatgtgaag agagaaatgc tcagggtatg tgttccttgg ctggtttcac tcaaatcgtt    1200
aacgaagcta gaatcccagc ttgttccttg tagtaa                              1236
```

<210> SEQ ID NO 32
<211> LENGTH: 410
<212> TYPE: PRT
<213> ORGANISM: Artificial Sequence
<220> FEATURE:
<223> OTHER INFORMATION: Sequence synthetically translated from SEQ ID NO: 31

<400> SEQUENCE: 32

```
Gln Ser Glu Pro Glu Leu Lys Leu Glu Ser Val Val Ile Val Ser Arg
  1               5                  10                  15

His Gly Val Arg Ala Pro Thr Lys Phe Thr Gln Leu Met Gln Asp Val
                 20                  25                  30

Thr Pro Asp Ala Trp Pro Thr Trp Pro Val Lys Leu Gly Glu Leu Thr
             35                  40                  45

Pro Arg Gly Cys Glu Leu Ile Ala Tyr Leu Gly His Tyr Trp Arg Gln
         50                  55                  60

Arg Leu Val Ala Asp Glu Leu Leu Pro Lys Cys Gly Cys Pro Gln Ser
 65                  70                  75                  80
```

```
Gly Gln Val Ala Ile Ala Asp Val Asp Glu Arg Thr Arg Lys Thr
                 85                  90                  95

Gly Glu Cys Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Cys Ile
    130                 135                 140

Leu Glu Arg Ala Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Cys Thr Pro Cys Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Cys Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gly Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 33
<211> LENGTH: 1236
<212> TYPE: DNA
<213> ORGANISM: Artificial Sequence
<220> FEATURE:
<223> OTHER INFORMATION: Synthetically generated DNA encoding a modified
      enzyme

<400> SEQUENCE: 33
cagagtgagc ctgagttgaa actggaatcc gttgtcatcg tctctagaca tggtgttaga      60
gcaccaacca agttcaccca acttatgcaa gatgtcaccc cagacgcttg gccaacctgg     120
ccagtcaagc tgggtgaatt gacacctaga ggttgtgagc tcattgctta cttgggtcac     180
```

```
tactggagac agcgtcttgt tgccgacgaa ttgttgccta agtgtggttg tccacaatct    240
ggtcaagtag ctattattgc tgacgtcgac gaaagaaccc gtaagacagg tgaatgtttc    300
gccgccggtc ttgctcctga ctgtgccatt accgttcacc atcaagctga cacttcttct    360
ccagatccat tgttcaaccc tttgaagact ggtgtttgcc aattggacgt tgctaacgtt    420
actagatgta tcttggaaag agctggagga tctattgctg acttcaccgg tcactaccag    480
actgccttca gagagttgga aagagttctt aacttcccac aatccaactt gtgccttaag    540
cgtgagaagc aagacgaatc ctgttccttg actcaagcat taccatctga gttgaaggtc    600
tccgccgaca acgtctcttt gaccggtgct gtcagcttgg cttccatgtt gactgaaatc    660
tttcttctgc aacaagctca aggtatgcct gagccaggtt ggggtagaat caccgactct    720
caccaatgga cacctttgtt gtccttgcac aacgctcaat tcgatttgct gcagagaact    780
ccatgtgttt gtagatccag agccaccccca ttgttggact tgatcaagac tgctttgact    840
cctcacccac tcaaaagca agcctacggt gttaccttgc ccacttctgt cttgttcatt    900
gccggtcacg atactaactt ggcatgtctc ggcggtgctt tggagttgaa ctggactctt    960
cctggtcaac tgataacac tccaccaggt ggtgagctcg ttttcgaaag atggcgtaga   1020
ctatctgata actctcaatg gattcaggtt tcgttggtc tccaaacttt gcagcagatg   1080
agagacaaga ctccactgtc tttgaacacg cctccaggag aagtcaaatt gaccttggct   1140
ggatgtgaag agagaaatgc tcagggtatg tgttccttgg ctggtttcac tcaaatcgtt   1200
aacgaagcta gaatcccagc ttgttccttg tagtaa                             1236
```

<210> SEQ ID NO 34
<211> LENGTH: 410
<212> TYPE: PRT
<213> ORGANISM: Artificial Sequence
<220> FEATURE:
<223> OTHER INFORMATION: Sequence synthetically translated from SEQ ID
    NO: 33

<400> SEQUENCE: 34

```
Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Cys Glu Leu Ile Ala Tyr Leu Gly His Tyr Trp Arg Gln
        50                  55                  60

Arg Leu Val Ala Asp Glu Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Cys Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Thr Arg Cys Ile
    130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175
```

```
Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Cys Val Cys Arg Ser Arg Ala Thr Pro Leu Leu
            260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Cys Leu Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
        370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410
```